United States Patent

Rasmussen et al.

Patent Number: 5,133,733
Date of Patent: Jul. 28, 1992

[54] COLLAPSIBLE FILTER FOR INTRODUCTION IN A BLOOD VESSEL OF A PATIENT

[75] Inventors: Erik Rasmussen, Soborg, Denmark; Rolf W. Günther, Aachen, Fed. Rep. of Germany

[73] Assignee: William Cook Europe A/S, Denmark

[21] Appl. No.: 606,588

[22] Filed: Oct. 31, 1990

[30] Foreign Application Priority Data

Nov. 28, 1989 [GB] United Kingdom ............... 8926857

[51] Int. Cl.⁵ .................................. A61B 17/00
[52] U.S. Cl. ......................................... 606/200
[58] Field of Search ............ 606/200, 127, 169, 198, 606/159

[56] References Cited

U.S. PATENT DOCUMENTS

| | | | |
|---|---|---|---|
| 2,281,448 | 4/1942 | Mathey | 220/86 |
| 3,334,629 | 8/1967 | Cohn | 128/325 |
| 3,540,431 | 11/1970 | Mobin-Uddin | 128/1 |
| 3,868,956 | 3/1975 | Alfidi et al. | 128/345 |
| 3,952,747 | 4/1976 | Kimmell, Jr. | 128/303 |
| 4,425,908 | 1/1984 | Simon | 128/1 |
| 4,494,531 | 1/1985 | Gianturco | 128/1 |
| 4,619,246 | 10/1986 | Molgaard-Nielsen et al. | 128/1 |

Primary Examiner—Michael H. Thaler
Attorney, Agent, or Firm—Woodard, Emhardt, Naughton, Moriarty & McNett

[57] ABSTRACT

In a collapsible filter for introduction into a blood vessel of a patient and of the kind comprising a number of legs (1–4) diverging from an apical hub (5) and each having a reversely turned hook (1b–4b) at its distal end with respect to said hub (5), each leg comprises a central element (1a–4a), bent into a smooth quasi-half sinusoidal form, and two substantially symmetrical curved side elements (1c–4c, 1d–4d) extending on either side of the central element (1a–4a). The filter may as whole may be unfolded from a collapsed insertion condition in which the central and side elements of all legs (1–4) forms a narrow bundle for arrangement in a catheter like insertion instrument into a tulip like filter configuration with the side elements (1c–4c, 1d–4d) interposed between the central elements (1a–4a) of the legs.

10 Claims, 1 Drawing Sheet

COLLAPSIBLE FILTER FOR INTRODUCTION IN A BLOOD VESSEL OF A PATIENT

BACKGROUND OF THE INVENTION

The present invention relates to a collapsible filter for introduction into a blood vessel of a patient and of the kind comprising a number of legs diverging from an apical hub and each having a reversely turned hook at its distal end with respect to said hub.

The invention is particularly, but not exclusively concerned with so-called vena cava filters intended for introduction into the vena cava, particularly the inferior vena cava, to entrap thrombi or emboli in the blood flow through the vein and prevent them from reaching the patients lungs and causing pulmonary embolization.

Such filters are known in a variety of different types as disclosed e.g. in U.S. Pat. Nos. 3,540,431, 3,952,747 and 4,619,246.

U.S. Pat. No. 3,540,431 discloses the so-called Mobbin-Uddin or MU-Filter which comprises a skeletal body of spoke shaped members inclined in a generally axial direction and a canopi of filtering media covering the struts and spanning the space between them.

Since the canopy portion has the effect of closing a major part of the vena cava this filter type is no longer much in use.

Another filter type is the so-called Kimray-Greenfield filter disclosed in U.S. Pat. No. 3,952,747, which contain a rather comprehensive analysis of the background and the state of the art. This filter device offers the advantage of a very moderate reduction of the cross-sectional area of the vein combined with a high filter efficiency, but suffers from the disadvantage of requiring a rather high caliper of the insertion instrument.

The latter disadvantage is avoided in the so-called Günther filter disclosed in U.S. Pat. No. 4,619,246, which comprises a collapsible basket assuming in its expanded state the shape of an apertured elongated solid of revolution with a number of anchoring legs extending from one end of the filter basket.

A disadvantage of the Günther filter is its considerable axial length, which may cause difficulties in the insertion operation.

SUMMARY OF THE INVENTION

It is the object of the invention to provide a filter of the kind mentioned, in which the abovementioned disadvantages have been eliminated or at least substantially reduced to provide a high efficiency filter of a simple construction and having a relatively short axial length with a moderate reduction of the blood flow area of the vein, whereas in its collapsed state the filter is concentrated into a slender and very narrow bundle of filter elements allowing for a correspondingly slender and narrow insertion catheter.

To accomplish these objects a collapsible filter according to the invention is characterized in that each leg comprises a central element, bent into a smooth quasi-halfsinusoidal form, and two substantially symmetrical curved side elements extending on either side of the central element whereby the filter as a whole may be unfolded from a collapsed insertion condition in which the central elements and side elements of all legs forms a narrow bundle for arrangement in a catheter like insertion instrument into a tulip like filter configuration with the side elements interposed between the central elements of the legs to assume the shape of an apertured solid of evolution with one pointed end at said hub.

As a result of this configuration the cross-sectional dimension of the filter in its collapsed state will correspond substantially to the sum of the thicknesses of the central and side elements of all the legs.

In the unfolded tulip-like configuration the filter has entrapping and blood flow properties, which are at least equal to what can be obtained by the most efficient prior art filters.

Moreover as a result of the tulip-like shape the distal ends of the filter legs will engage the wall of the vein along a certain length. Thereby the risk of perforation of the wall which has occured with some prior art filters is minimized and the filter is held centralized in the vein during implantation as well as afterwards in case of movements.

Since the wall of the vein is acturally contacted by the distal end of the "blades" formed by the central and side elements of the legs an optimum possibility for filter ingrowth in the veinwall is obtained and thereby an optimum long term security against migration of the filter.

BRIEF DESCRIPTION OF THE DRAWINGS

In the following the invention will be further explained with reference to the accompanying drawings in which.

DESCRIPTION OF THE PREFERRED EMBODIMENT

Figure 1:
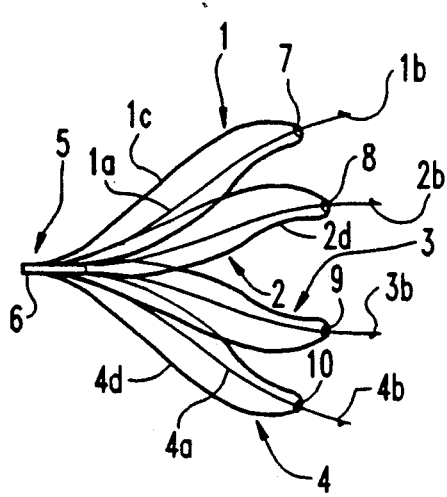
FIGS. 1 and 2 show an embodiment of a filter according to the invention in its unfolded state.

In the embodiment shown the filter comprises four legs 1, 2, 3 and 4 diverging from an apical hub 5 at which the legs 1 to 4 are held together by an end ferrule 6 of the kind e.g. disclosed in U.S. Pat. No. 4,619,246.

Each leg comprises a central element 1a, 2a, 3a, and 4a bent into a smooth quasi-halfsinusoidal form and having a reversely turned anchoring hook 1b, 2b, 3b and 4b at its distal end with respect to hub 5 as well as two symmetrical curved side elements 1c, 2c, 3c and 4c, and 1d, 2d, 3d and 4d extending on either side of the central element.

In the embodiment shown the two side elements of each leg 1 to 4 are formed from one piece of wire the ends of which are held together in hub 5, whereas at the middle of its length the wire piece forms an eyelet 7, 8, 9 and 10 surrounding the central leg element to be freely slidable along a part of the length thereof.

Figure 2:
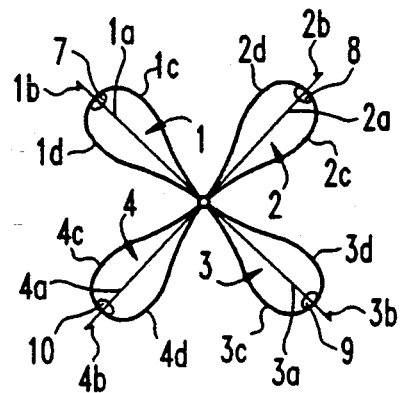
Figure 3:
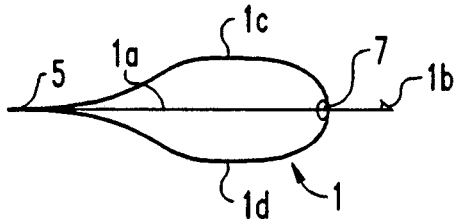
FIGS. 3 and 4 show a single leg of the filter in its unfolded state and an intermediate state between the unfolded and collapsed configurations, respectively.
Figure 5:
FIG. 5 shows the filter in its collapsed state.
Figure 4:
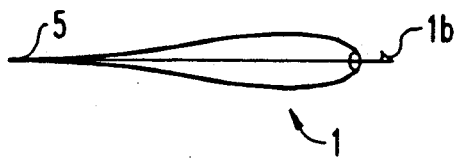

From the unfolded tulip-like configuration illustrated in FIGS. 1, 2 and 3 the filter may be collapsed into a slender and very narrow bundle of filter elements as shown in FIG. 5, the cross-sectional dimension of which is approximately equal to the sum of the thicknesses of the central and side elements of all four legs.

As best seen in FIG. 2 the side elements of each leg have a length and curvature such that in the unfolded tulip-like configuration of the filter the maximum distance between the side elements is of the same order as the distance between neighbouring side elements of two adjacent legs. Moreover, the length and curvature is preferably chosen such that after insertion into the vena cava inferior the eyelets 7-10 will be positioned substantially at the inner side of the wall of the blood vessel.

As best seen in FIG. 1 the filter according to the invention has in its unfolded state a relatively short axial length of the same order as the diameter of the filter whereby proper arrangements of the filter into the inferior vena cava is facilitated.

Whereas the invention has been described and illustrated with reference to a specific embodiment having four legs it will be understood that various modification, e.g. with respect to the number of legs can be made without departing from the scope of the following claims.

We claim:

1. A collapsible filter for introduction into a blood vessel of a patient comprising a plurality of legs diverging from an apical hub and each of said plurality of legs having a reversely turned hook at their respective distal ends with respect to said hub, wherein each of said plurality of the legs comprise a central element, and two curved side elements extending on either side of the central element, wherein the curved side elements of each leg are formed from one piece of wire the ends of which are joined together at the apical hub, whereby the filter as a whole may be unfolded from a collapsed insertion condition in which the central elements and side elements of the legs form a narrow bundle for arrangement in a catheter like insertion instrument into a tulip like filter configuration with the side elements interposed between the central elements of the legs.

2. A collapsible filter as claimed in claim 1 in wherein the collapsed insertion condition the side elements of each leg extend in substantially parallel juxtaposed relationship with the central element.

3. A collapsible filter as claimed claim 1 wherein the unfolded tulip-like configuration of the filter the maximum distance between the two side elements of each leg midway between the apical hub and the eyelet is of the same order as the distance between neighboring side elements belonging to two adjacent legs.

4. A collapsible filter for introduction into a blood vessel of a patient comprising a plurality of legs deverging from an apical hub and each of said plurality of legs having a reversely turned hook at their respective distal ends with respect to said hub, wherein each of said plurality of the legs comprise a central element bent into a smooth quasi-halfsinusoidal form, and two curved side elements extending on either side of the central element, whereby the filter as a whole may be unfolded from a collapsed insertion condition in which the central elements and side elements of the legs form a narrow bundle for arrangement in a catheter like insertion instrument into a tulip like filter configuration with the side elements interposed between the central elements of the legs, wherein the curved side elements of each leg are formed from one piece of wire the ends of which are joined together at the apical hub, whereas at the middle of its length said piece of wire forms an eyelet surrounding the central element to be freely slidable along a part of the length thereof.

5. A collapsible filter as claimed in claim 4 wherein in the collapsed insertion condition the side elements of each leg extend in substantially parallel juxtaposed relationship with the central element.

6. A collapsible filter as claimed in claim 5 wherein in the unfolded tulip-like configuration of the filter the maximum distance between the two side elements of each leg midway between the apical hub and the eyelet is of the same order as the distance between neighboring side elements belonging to two adjacent legs.

7. A collapsible filter as claimed in claim 5 wherein the side elements of each leg have a length and curvature such that in the unfolded configuration the eyelet will be positioned substantially at an inner side of the wall of a vena cava in which the filter is inserted.

8. A collapsible filter as claimed in claim 4 wherein the side elements of each leg have a length and curvature such that in the unfolded configuration the eyelet will be positioned substantially at an inner side of the wall of a vena cava in which the filter is inserted.

9. A collapsible filter as claimed claim 8 wherein in the unfolded tulip-like configuration of the filter the maximum distance between the two side elements of each leg midway between the apical hub and the eyelet is of the same order as the distance between neighboring side elements belonging to two adjacent legs.

10. A collapsible filter as claimed claim 4 wherein in the unfolded tulip-like configuration of the filter the maximum distance between the two side elements of each leg midway between the apical hub and the eyelet is of the same order as the distance between neighboring side elements belonging to two adjacent legs.

* * * * *